US005360607A

United States Patent [19]

Eyal et al.

[11] Patent Number: 5,360,607

[45] Date of Patent: Nov. 1, 1994

[54] METHOD FOR PRODUCTION AND USE OF PATHOGENIC FUNGAL PREPARATION FOR PEST CONTROL

[75] Inventors: Jacob Eyal, Baltimore; James F. Walter, Ashton, both of Md.; Osborne, Lance, Longwood, Fla.; Zdenek Landa, Ceske Budejovice, Czechoslovakia

[73] Assignee: W. R. Grace & Co.-Conn., New York, N.Y.

[21] Appl. No.: 850,330

[22] Filed: Mar. 10, 1992

Related U.S. Application Data

[63] Continuation-in-part of Ser. No. 772,983, Oct. 7, 1991, abandoned, which is a continuation-in-part of Ser. No. 639,641, Jan. 10, 1991, abandoned.

[51] Int. Cl.[5] .......... C12N 1/14

[52] U.S. Cl. .......... 424/93.5; 424/493; 435/174

[58] Field of Search .......... 424/93 Q, 493; 435/174

[56] References Cited

U.S. PATENT DOCUMENTS

| | | | |
|---|---|---|---|
| 4,530,834 | 7/1985 | McCabe et al. | 424/93 Q |
| 4,668,512 | 5/1987 | Lewis et al. | 424/93 Q |
| 4,718,935 | 1/1988 | Walker et al. | 424/93 Q |
| 4,724,147 | 2/1988 | Marois et al. | 424/93 Q |
| 4,942,030 | 7/1990 | Osborne | 424/93 R |
| 5,074,902 | 12/1991 | Connick, Jr. et al. | 424/93 Q |

FOREIGN PATENT DOCUMENTS 268177 5/1988 European Pat. Off. .

OTHER PUBLICATIONS

Ignoffe et al., Handbook of Natural Pesticides, V, Part A.

McCoy et al., Microbial Insecticide, 1988, CRC Press.

Burge, Fungi in Biological Control Systems, 1988, Manchester Univ. Press.

Ferron, Annual Review of Entomology, vol. 23, pp, 409–442, 1978.

Kodaira, Agr. Biol. Chem., pp. 26–36, 1962.

Suzuki et al., Agr. Biol. Chem., vol. 35 pp. 1641–1643, 1971.

McDonald et al., Vth Intl. Colloquium Invertebr. Pathology and Microb. Control, p. 147, 1990.

Roberts et al. Vth Intl. Colloquium Invertebr. Pathology and Microb. Control, p. 336, 1990.

Lewis et al., Proceed. Int. Symp. Control. Rec. Bioact. Mater, vol. 12, pp. 341–343 1985.

Fravel et al., Phytopathology, vol. 27, pp. 3341–3348, 1982.

Cabinillar, Factors Influenc. Efficacy/Paecilom. lilacinus/Biocont., 1987.

*Primary Examiner*—Irene Marx

*Assistant Examiner*—Jean D. Witz

*Attorney, Agent, or Firm*—Beverly K. Johnson

[57] ABSTRACT

The present invention provides a process, formulations, and method of using novel biopesticides comprised of a prilled formulation comprising a carrier and a pathogenic fungal mycelium.

20 Claims, 3 Drawing Sheets

METHOD FOR PRODUCTION AND USE OF PATHOGENIC FUNGAL PREPARATION FOR PEST CONTROL

This application is a continuation-in-part application of U.S. Ser. No. 772,983, filed Oct. 7, 1991, abandoned which is a continuation-in-part of U.S. Ser. No. 639,641, filed Jan. 10, 1991, abandoned.

TECHNICAL FIELD

The present invention relates to novel methods and fungal compositions for the biocontrol of pests. More specifically, the present invention relates to novel entomogenic fungi biopesticidal compositions, the method of producing the same, and the method of using the same for the control of pests. The biopesticides are particularly useful in controlling pests which cause significant amount of damage to plants (e.g. soilborne pests and plant pests). A preferred entomogenic fungus useful in the present invention is *Paecilomyces fumosoroseus* ATCC 20874.

The invention also provides novel methods for preparing and preserving fungal biopesticidal materials, and methods of applying and using such biopesticidal formulations to obtain maximum efficiency in controlling various soilborne pests, plant pests, mosquitoes and soil nematodes. Methods for effective quality control of biopestices disclosed herein are also provided.

BACKGROUND

Chemical pesticides have been used intensively to control pests for many years. An awareness of recent problems in the use of pesticides and concern about their adverse effects on man and his environment have resulted in more commercial attention being given to biological control alternatives. Certain entomogenic fungi have been recognized by researchers to be pathogenic to different pests; particularly the use of entomogenic fungi has been widely studied as biological control agents in the USSR and in Europe. Update reviews on the different pathogenic fungi and their use and status can be found in: Carlo M. Ignoffo and B. Handava "Handbook of Natural Pesticides", vol. V, part A., C. W. McCoy et al. "Microbial Insecticide", CRC Press, 1988, and M. N. Burge "Fungi in Biological Control Systems", Manchester University Press, 1988. Unlike insect pathogenic bacteria or other microorganisms (e.g., viruses or protozoa) which must be ingested by the insect to initiate diseases, entomogenic fungi normally invade through the host's cuticle.

Entomogenic fungi infect pests, usually insects, by a parasitism disease mechanism. The infection process development is believed to consist of the following steps:

1. Attachment—The conidium of the entomogenic fungi spore is attached to the insect cuticle.
2. Germination—The conidia spore is germinated on the insect cuticle to form a germ tube.
3. Penetration—The germ tube penetrates directly into the cuticle. It is believed that the cuticular invasion involves both enzymatic and physical activities.
4. Growth—The fungus grows in the hemocoel as mycelium or blastospore. The fungi overcome the host by invasion of organs.
5. Saprophytic Growth—The fungi grows on the outside of the insect and produces aerial conidia spores.

Some entomogenic fungi overcome their host before extensive invasion of organs takes place, presumably by production of toxins. Although toxic compounds have been reported from culture filtrate of mycelium of several entomogenic fungi (e.g., *Paecilomyces fumosoroseus* was shown to produce the toxin Beauvericin (Ferron, Annual Review of Entomology 23:409–442 (1978), and a peptide toxin known as destruxin A has been isolated from culture broth of *Metarrhizium anisoplia* (Y. Kodaira, Agr. Biol. Chem. Chem. 26–36 (1962)), only in few cases it was reported that toxins have been detected in insects infected with the entomogenic fungi (Suzuki et al., Agric. Biol. Chem. 35:1641–1643 (1971)).

The use of the entomogenic fungi for control of different pests is not itself a new idea. Entomogenic fungi such as Metarrhizium, Beauveria, Hirsutella, Verticillium or Paecilomyces have been studied for development as pest control agents. Solid state fermentation has been widely examined because this method allows the production of the infectious bodies of the entomogenic fungi, e.g., conidia spores. However, it has been found that conidia spores of the various entomogenic fungi are very sensitive to drying processes and the conidia spores lose their viability very quickly.

Submerged fermentation have significant problems to overcome. Most of the entomogenic fungi heretofore grown in submerged culture produce mostly blastospores with some mycelium. Blastospores are not stable during storage or drying processes. Attempts to formulate blastospores resulted in reduced efficacy and stability.

In order to overcome the above stability problems associated with conidia spores and blastospore preparations, several processes have been disclosed in the literature for the production of biocontrol agents based on biomass obtained from submerged culture fermentation. These techniques generally involve growing fungi in liquid media followed by inoculation of a solid media or an inert carrier, such as vermiculite, on which the conidia spores are produced. For example, Kybal (1976) discloses a process for incubating biomass containing mycelium, blastospores and other fungal stages in shallow, aerated vessels to produce conidia spores directly on the surface of the coated vessel surface. However, this process is very labor intensive and the conidia spores obtained is only on the vessel surface. The surface area per apparent volume tends to be small and the efficiency is low.

In another process McCabe et al., (U.S. Pat. No. 4,530,834), discloses the use of entomophthoralean mycelium produced in submerged culture for the production of resting conidia spores. This process is a diphasic system whereby production of spores or blastospores is bypassed. First, the biomass produced by liquid fermentation is dried with protective agents, and the dry biomass mat obtained is milled to a dry powder form. Next, the dry powder preparation is rewetted and applied to the target pest. However, this method is plagued with stability problems. The powder product needs to be stored below 4° C. to maintain its viability. Even under such storage conditions the product is only stable for 64 days. Further, conidia spores produced from reconstituted powder are short lived and fragile.

Dried mycelium particles obtained from liquid fermentation of different entomogenic fungi have been produced in similar ways by different investigators. For example, McDonald et al. (Vth International Colloquium on Invertebrate Pathology and Microbial Control, Adelaide, Aus, p. 147) disclose a similar basic process for the entomogenic fungus *Culicinomyces clavisporus* for mosquito control. This process involves growing the fungus in liquid culture for 6 days, harvesting the suspension by filtration and adding sucrose followed by air drying. The dried mycelial mat was then ground in a hammer mill and sieved through a 3.5 μm sieve. Upon addition of these mycelium particles to water approximately $5\times10^6$ conidia spore/mg of dried particle were produced. Dried mycelium particles could be stored for 1-5 weeks at 4° C. without losing activity. A similar approach has been used by Roberts et al. (Vth International Colloquium on Invertebrate Pathology and Microbial Control, Adelaide, Aus, p. 336) for the use of dried mycelium particles of *Metarrhizium anisopliae* isolate ARSEF 2457 to control the Japanese beetle and other pests. Based on the Roberts et al. results it has been found that lyophilized Metarrhizium mycelium has a longer shelf life in soil than conidia spores.

Bayer A. G. (EP application 0268117 A2, 1987) has reported on a similar method which is based on the production of mycelium and blastospores of *Metarrhizium anisopliae* in a fermenter. During the course of fermentation, the mycelium/blastospore aggregate to form pellets in the size of 0.1 mm up to 1.5 mm in diameter. At the end of the submerged culture fermentation, the mycelium/blastospore aggregates are harvested and dried in a fluidized bed dryer to form a final product which consists of dry mycelium/blastospore granules with 0.5 to 1.5 mm diameters. The granules can be applied to soil where they can form infectious conidia spores. However, this method suffers from several problems. First, the fungal pellets formed in the fermenter result in a very low biomass yield. Therefore, such a fermentation process is not economical. Also, the final granular product obtained must be stored under vacuum and at a low temperature. It seems also that the conidia spores formed after activation in the soil have a short life. This is probably because the granules do not contain any nutrients which can stimulate or promote growth.

Another approach, which has been used widely for the delivery of different fungal pathogens (mainly conidia spores and chlamydospores) against plant diseases, is encapsulating fungal spores in alginate prills (Lewis et al., Proceed. Intern. Symp. Control. Recs. Bioact. Mater, 12:341-3 (1985), Fravel et al., Phytopathology, 27:3341-8 (1982), and J. J. Morois, U.S. Pat. No. 4,724,147). This method has been ignored in general for the delivery of entomogenic fungi for insect and other pest control. Few publications on the use of alginate prill for delivery of entomogenic fungi are known. For example, Enrique A. Cabanillar (Ph.D. thesis) "Factors Influencing the Efficacy of *Paecilomyces lilacinus* in Biocontrol", 1987, North Carolina State University, described this method to deliver conidia spores of *Pacilomyces lilacinus* produced on solid media (solid state fermentation) against Koot-knot nematode. Roberts, et al. (Entomopathogenic Fungi: Recent Basic & Applied Research; Matha, V. et al. (ed) Biopesticides Theory & Practice Proc. Conf., Sep. 25-28, 1989, Ceske, Budejovice, Czechoslovachia 11-30 pp) disclose a process for using alginate pellets which incorporate the mycelium biomass of *Beaveria bassiana* & *Metarrhizium anisopliae* with pre-gelatinized starch as a basic nitrogen supply.

SUMMARY OF THE INVENTION

This invention provides a process and formulation for the production of biopesticides comprising mycelium and conidia spores of entomogenic fungi. The process offers a new opportunity to use entomogenic fungi in the control of soil pests, plant pests, nematodes, and mosquitos. The method of the invention is particularly useful to prepare pesticidial compositions comprising the entomogenic fungus *Paecilomyces fumosoroseus* ATCC 20874 (U.S. Pat. No. 4,942,030). However, a variety of fungi having pesticidal properties can be used in the process and formulations of the invention to control various pests.

This invention provides a process for preparing a biopesticide useful for controlling or preventing pest infestation. The process includes fermenting one or more species of fungus effective for control of pests in a culture medium by submerged fermentation to produce biomass such that at least about 80%, preferably 90% and most preferably 95% of the biomass is in the form of mycelium. The mycelium is then harvested and mixed with a carrier. The biomass/carrier mixture is formed into prill and dried. The prill can be either used directly as a dry formulation or the prill can be used as a carrier for sporulation of conidia spores (reactivated prill) or the harvested conidia spores can be used or the harvested conidia spores can be pregerminated and then used.

Generally, this method comprises the production of mycelium prills of the entomogenic fungi. The process for forming prills is divided into three main stages as follows:

Stage I: Production of fungal biomass in very high yield in fermenter in the form of filamentous mycelium.

Stage II: Harvesting the filamentous mycelium, formulating the wet mycelium, and encapsulating the formulated wet mycelium in calcium alginate prills.

Stage III: Drying the formulated prills and packaging the product for use as a biopesticidal agent.

The method can further comprise the following stages:

Stage IV: Activating and cultivating the prill to produce pathogenic conidia spores.

Stage V: Drying the reactivated prill and packaging the product for use as a biopesticidal agent.

It is within the scope of the invention to dry the prill before or after activating and culturing the formulated prill.

The method can further comprise the following stage:

Stage VI: Harvesting the pathogenic conidia spores from the reactivated prill and using the conidia spores as a biopesticidal agent.

The method can further comprise the following stage:

Stage VII: Pregermination of the pathogenic conidia spores harvested from the reactivated prill and using the pregerminated conidia spores as a biopesticidal agent.

For purposes of this invention, the term "biopesticide" or "biopesticidal agent" shall mean a biologically-active pathogenic fungal agent which is useful in the control or prevention of plant-, soil- or water-borne pest infestation by adversely affecting the existence or growth of the target pest, particularly insects. Such control can comprise a complete killing action, eradication, arresting in growth, reduction in number, induction of plant resistance or the production of phytoalexins or any combination of these actions. The term "entomogenic" as employed in the specification and claims of this invention shall mean pathogenic to insects specifically but can also be construed broadly to mean pest pathogen. The term "control" or "biocontrol" as employed in the specification and claims of this invention is to be construed as meaning protecting plants, soil or water from pest, particularly insect, damage by use of the biopesticides of this invention. The term "pesticidally effective amount" or "effective amount" is used herein to mean the amount of biopesticide sufficient to control pests, in particular insects.

As described in the background, at present there is no effective stable delivery system available for entomogenic pesticides.

A primary object of this invention is to provide a process for producing an economical entomogenic fungal biopesticide product. The process produces a fungal biocontrol material that is easy to handle and to apply in either horticultural or agricultural settings. The dried fungal product prepared as described herein is easily produced, stored, shipped, and formulated to control plant, soil, and water pests. The product can be stored at room temperature, preferably between 10° to 25° C., for extended periods, i.e., more than a year, without losing conidiation activity and prill/spore viability.

Still another object of this invention is to provide a process of converting an actively growing culture of an entomogenic fungus into a formulated biopesticide which is easily handled and applied. The formulated prill of the invention maintains biological activity of the fungal product until the time of application. Without the prill formulation, the mycelium could not survive under such conditions. Upon application to to a desired locus and upon rewetting, the dried prill is "activated", or reconverted into a biologically active form, in which mycelium budding from the prill occurs in less than 48 hours after wetting. As the mycelium budding begins consuming the nutrients provided by the prill formulation, conidiation begins, resulting in the production of conidia spores. Conidia spores are the biologically active form of the fungus which is pathogenic to pests.

Another object of this invention is to provide a reactivated carrier which is suitable for efficiently sporulating a culture of the entomogenic fungus to produce conidia spores in high concentrations. The conidia spores produced from the reactivated carrier have high viability and infectivity and are produced in higher concentrations than previously known methods. Upon harvest, the conidia spores can be applied directly to the plant, soil, seed or root with or without formulation material. Either reactivated or non-activated carrier, i.e., prill, can be applied to soil. Further, the conidia spores harvested from activated prill can be transferred into a aqueous suspension and applied to the locus of the plant. For purposes of this invention, the term "locus" is used to describe the location wherein treatment is desired. The locus may be in or on the surface of the soil, on the plant itself or on the seed or root thereof, or on the surface of water.

Another object is to provide a method to pregerminate the active conidia spores harvested from the prill and apply the pregerminated spores directly to the plant locus with or without formulation material.

Another object of this invention is to provide a biopesticide formulation/carrier that is useful in the prevention or control of pest infestation, including, but not limited to, plant and soil-borne insects and nematodes and water pests, such as mosquitos. An additional objective of the present invention is to provide an alternative to chemical pesticides.

It is a further object of this invention to provide a method for utilizing as a biopesticide a selected strain of the entomogenic fungal, species *Paecilomyces fumosoroseus* ATCC 20874 (PFR) which has a high level of infectivity for different plant pests. It is still a further object of this invention to provide a biopesticide containing a selected strain of the fungal species PFR which can be readily mass produced as required for horticultural and agricultural applications.

Another object of this invention is to provide a biopesticidal preparation comprising a fungal mycelium preparation of *Paecilomyces fumosoroseus* which is produced in a submerged culture. The mycelium is combined with a carrier. The mycleium/carrier mixture is then prilled to provide high quality control, stability, shelf life, infectivity, and specificity in infecting various plant pests.

Another object of the invention is to provide an economical method for efficiently culturing fungal spores for field or greenhouse application. The method of the invention enables the production and use of large volumes of biopesticide in an easy and convenient manner.

Still another object of this invention is to provide a novel method for providing pathogenic fungal conidia spore biopesticide having improved stability, viability any pathogenicity over longer periods of time than conidia spore or fungal matter produced by previously known methods. The method provides major economical and commercial advantages in the storage, delivery and application of such a biopesticide.

It is further an object of the invention to provide a method of storing and delivering the sporulated reactivated biopesticides of the invention by placing the reactivated prill having conidia spores attached in a water-soluble polymeric container. Pesticidal formulations of the invention are prepared by dissolving the polymeric container plus biopesticide in an aqueous solution. A novel composition of water-soluble polymeric container and reactivated prill, and the method of use thereof are to prepare novel biopesticidal formations are also provided.

DETAILED DESCRIPTION OF THE INVENTION

Figure 1:
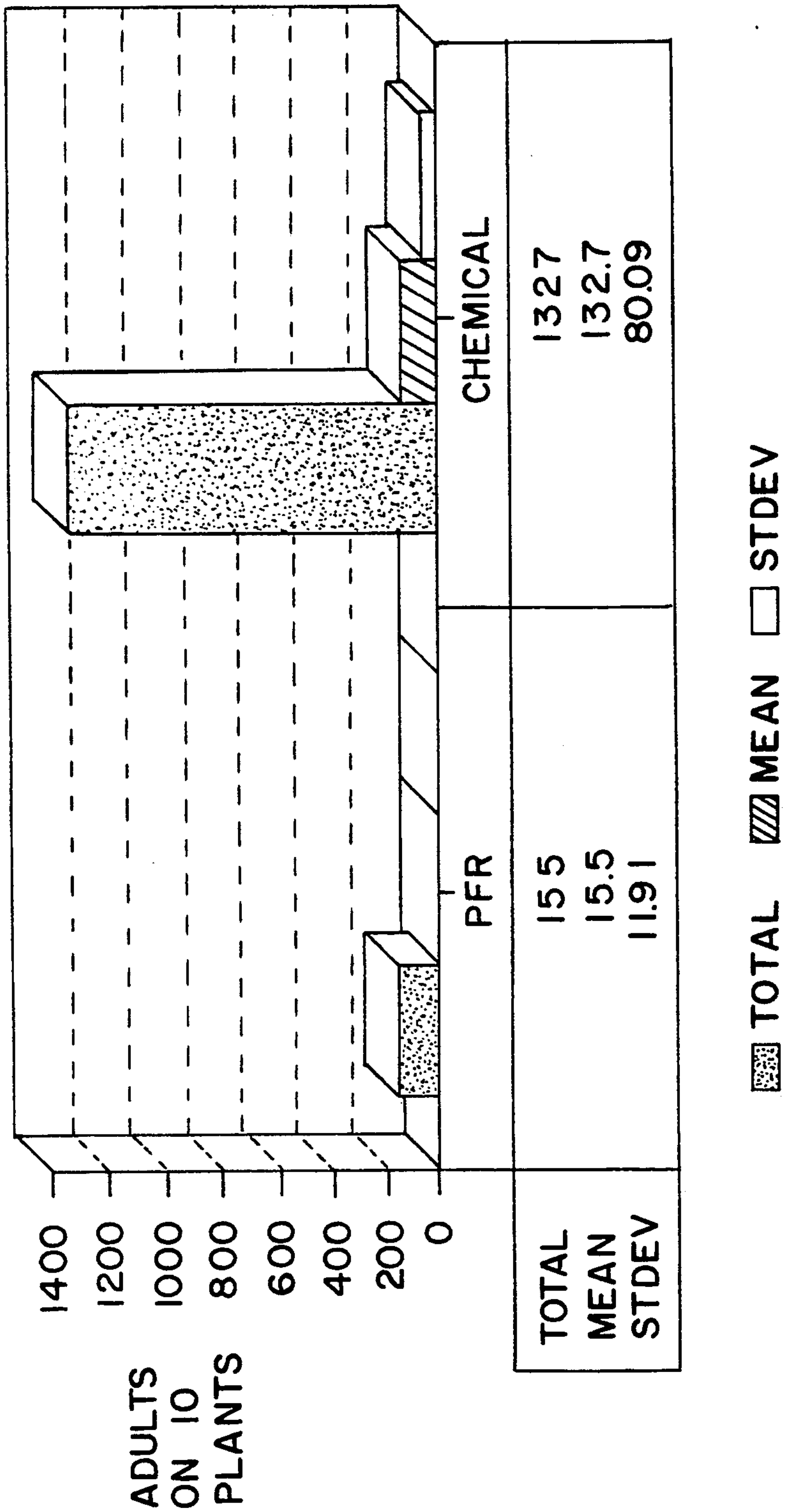
FIG. 1 compares the biological control of adult whiteflies using formulation of the invention vs. chemical treatments.

The invention disclosed herein is a process and method for preparing a biopesticide agent which can be applied to plants, in and/or on the surface of soil for the control of plant pests, particularly insects, or on the surface of water to control pests such as mosquitos. The pathogenic fungi which are useful for the purpose of this invention are preferably the fungal species from the taxonomic classes as described by Ainsworth et al. "The Fungi", vol. 4 a,b., Academic press (1973). The major Taxa which contain the entomogenic fungal species are from the following subdivisions: Zygomycotina, Mastigomycotins, Ascomycotina, Basidiomycotina, and Deuteromycotina. These different subdivision can be presented also by the different classes: Chytridiomycetes, Oomycetes, Zygomycetes, Plectomycets, Pyrenomcetes, Loculoascomycets, Teliomycetes, Coelomycetes, and Hyphomycetes.

Fungi from these classes which produce pathogenic spores that are infective to pests can be used. For example, the following entomogenic fungi are considered to be the most suitable for pest control: Aspergillus, Aschersonia, Massospora, Beauveria, Metarrhizium, Verticillium, Paecilomyces, Hirsutella, Nomuraea, Hymenostilbe, Cordyceps, Coelomomyces, Lagenidium, Leptolegnia, Conidiobolus, Zoophthora, Culicinomyces, and Tolypocladium. Numerous strains of these entomogenic fungi exhibit pathogenic activity against plant pests, mosquitos, and other animal pests. Most preferred are, the entomogenic fungi Paecilomyces, particularly the species *Paecilomyces fumosoroseous* ATCC 20874. This particular strain is well suited for use as a biopesticide according to this invention.

FERMENTATION

The fungal biopesticides of the invention are prepared for delivery by growing selected fungal strain or strains, particularly the preferred *Paecilomyces fumosoroseous* strain ATCC 20874, in submerged culture. Although this description refers to the preparation of a single fungus, it will be appreciated that a mixture of genera or species may be desirable in some applications. An inoculum of the preferred fungus or fungi may be prepared by a standard surface culture method in which the preferred strain is grown on an agar slant, and the agar content is used to inoculate shake flasks containing agar nutrient under standard conditions. After 48 hours of incubation the shake flask contains mainly blastospores. This inoculum is used to inoculate fermenters using standard methods. It is within the scope of the invention to use any conventional inoculation method.

The fermentation is conducted in such a way that the biomass in the fermenter substantially or predominately comprises filamentous mycelium, at least about 80% mycelium, preferably at least about 90% mycelium, and most preferably at least about 95% mycelium. This can be achieved by supplying an excess of complex carbon and complex nitrogen sources. The complex carbon source can be naturally occurring mixtures such as molasses, and the complex nitrogen source can be corn steep liquor and/or cotton seed flour. Other known complex carbon and complex nitrogen sources can also be used. Supply of pure sugars such as sucrose, dextrose, glucose or other sugar sources will result in the formation of mainly blastospores and are therefore not preferred. The composition of the nutrient media can be varied over a wide range. However, the preferred nutrient solution contains about 4 to 8 wt % complex carbon source and about 0.5 to 5 wt % complex nitrogen source. The production of mycelium can also be intensified by the constant supply (fed batch addition) of molasses during the fermentation process. The fermentation can be carried out in batch, continuous or in fed batch mode.

In order to increase the yield of filamentous mycelium in the fermenter, it may be desirable to add stimulant nutrients to the cultivation media. Such stimulant nutrients include liquid fat, oils, surfactants, and polyacids such as linoleic acid, silicon oils, water emulsion, etc.

A fed batch fermentation process can be advantageous to use, especially when the pH of the fermentation is shifting toward acid conditions. By adding molasses or other suitable complex carbon sources, it is possible to maintain constant conditions in the fermentation without using large amounts of base for pH adjustment. Fed batch addition of molasses, for example, can be used as buffer control for the fermentation. Preferably, the addition Of molasses during fermentation is at a rate of about 1% molasses per 24 hours. Preferably, molasses addition begins after about 48 hours or when the pH shifts toward acidic conditions (below about pH 5.0).

The fermentation should be carried out in a manner such that agitation and aeration will be maximized. Any convenient means of aeration and agitation can be employed. If agitation is low, aggregation of mycelium occurs. Therefore a minimum agitation rate of about 400 rpm to 600 rpm is preferred with aeration in the order of about 0.8 to 1 vvm. The fermentation process preferably should be carried out in the temperature range of about 28°-30° C.

The fermentation should be carried out at an acidic pH sufficient to promote maximum formation of mycelium. Preferably, the pH is 4.0 to 6.0, most preferably about 5.0. Adjustment and control of the pH value can be achieved by the addition of an organic or inorganic base, preferably sodium hydroxide, ammonium hydroxide or any solution of triethyl amines.

In order to prevent developing undesirable amounts of foam during fermentation, standard chemical defoaming agents can be added. Standard chemical defoaming agents include silicon oil, polypropylene or glycol compounds, or other synthetic antifoams. The end of the cultivation can be easily determined by the standard method of biomass determination (e.g., dry mass determination). Cultivation time will vary depending upon such factors as, for example, the fungus or fungi used; the nutrients used; and the type of fermentation used. A 4 to 6 days cultivation typically will be sufficient to yield 30-50 g/liter of dry mycelium. This yield is sufficient for use in the formulation stage of this invention.

The separation of the filamentous mycelium biomass from the fermentation media can be accomplished by standard procedures such as filtration, centrifugation or other convenient means of separation. To avoid contaminating the mycelium with undesirable microorganisms, harvesting the mycelium under sterile conditions is recommended.

FORMULATION

In order to prepare the biopesticide formulation carrier of this invention, carrier materials are used which are capable of supporting fungal growth and promoting rapid sporulation. Suitable carriers include inert filling compounds such as clay, bentonite, talcum, perlite, peatmoss, diatomaceous earth, kaolin, vermiculite, bran, dry milk, and minerals. Vermiculite is preferred because it results in a stable biopesticide product and also because it lowers the density of the product, which allows the mycelium to conidiate faster. The vermiculite (or other carrier material) most preferably is pretreated to reduce the level of contaminating microorganisms. This preferably is by heating (i.e., at 100° C. or higher for at least up to about 1 hour) or may be by irradiation. Microbial decontamination may be also accomplished chemically, provided that there is no retained chemical interference with fungal viability and growth. Returning to the preferred embodiment, the filamentous mycelium biomass is then added to the vermiculite or other carrier component by mixing.

Nutrients can be included in the mycelium formulation. Such nutrient sources may include carbon and nitrogen sources such as molasses, whey, milk powder, cotton seed flour, different autolyzed peptone, bran, wheat, malt extract or yeast extracts. It may be desired to add stabilization and/or protective agents to the formulation, such as polyalcohols, glycerin or sugars. Antioxidants compounds such as ascorbic acid or propyl gallate may be added, if desired.

The formulated mycelium mixture is then prilled by methods known to one skilled in the art. The prilling process can be conducted by adding a prilling agent such as sodium alginate or potassium alginate to the biomass/carrier mixture and by dropwise adding the mixture to a coagulant bath containing calcium chloride or calcium gluconate. The sodium alginate concentration in the propagule mixture can vary from about 0.2 to about 3% depending on which formulation is used and degree of propagulation needed. Calcium chloride or calcium gluconate concentration for coagulating can vary from about 1 to about 15% w/v as needed for suitable prill formation. Coagulation proceeds faster when the concentration of salts in the coagulation bath is increased. The prill formed by this method can be dried immediately by using any convenient drying method, such as air drying or oven drying. However, a fluidized bed process is preferred to obtain flowable prill with uniform, physical characteristics (shape, mechanical strength, size, and density).

In order to increase the conidiation potential of the prill, it may be desired to add nutrients which will stimulate conidiation to the prill. Such stimulating material can contain natural food ingredients such as molasses, peptone, cotton seed flour, glucose solution, etc. The addition of the nutrient can be before drying or in the drying process. Addition of nutrients before drying can be achieved by submerging the prill in a concentrated nutrient solution until diffusion is complete and then drying the treated prill. Addition of nutrients in the drying process can be achieved by coating the prill during their movement in the fluidized bed. Such coating procedures are well known. The prill should be dried to a moisture or total volatiles content of about 2 to about 12% (w/w). However, a total volatiles content of about 6-8% is preferred. The moisture content can be easily determined according to standard methods using moisture balances. To avoid contamination with undesirable microorganisms, the drying process should be done in sterile air, for example by using air filters.

Prill produced according to the invention can be stored under dry conditions at temperatures between about 4° C. to about 25° C. To preserve the viability of the prill beyond 12 months, it is recommended to store the prill in a vacuum or in an inert atmosphere such as under argon, nitrogen or other inert gases.

For purposes of this invention the term "prill" is used to mean a stable, granulated particle or bead which does not produce a powder or dust and which has an average particle size of from about 0.2 mm to about 5 mm in diameter.

REACTIVATION AND HARVEST

The formulated prill can optionally be reactivated prior to use. The stable prill formulation can be reactivated prior to use to provide a concentrate of highly active, fresh conidia spores. The formulated prill contain optimum nutrients which stimulate sporulation and production of a large number of spores in a short time upon activation. Each prill (less than 1 mm diameter) can produce as much as $10^7$–$10^8$ conidia spores per prill and the conidia spores have high insecticidal effect on controlling pests. Reactivation is easily achieved by addition of moisture, preferably water, to the prill and allowing the growth of mycelia and production of conidia spores. Optimal growth conditions are incubation at about 20°–28° C., preferably about 25° C. for less than about seven days, preferably about 3 to about 5 days. Reactivation can take place in any suitable closed, sterile container, such as a petri dish or tray. The prill preferably should be placed as a monolayer in the container in order to achieve maximum surface area for the sporulation and germination process. The reactivated prill can be stored for prolonged periods of time, i.e., up to about 1 year at about 10° C. to about 25° C., without losing conidiation activity or spore viability.

The conidia spores can be easily harvested from the reactivated prill by washing with water or a non-toxic oil to provide aqueous or oil suspensions of conidia spores. Preferably, the aqueous suspension contains a surfactant. Any suitable surfactant can be used, such as, for example, a polyoxyethylene sorbitan monolaurate surfactant sold under tradenames Tween 80® or Tween 20® by Fisher Scientific of Fairlawn, N.J., in the range of 0.01–0.1%. Suitable oils include any oil which is non-toxic such as, for example, cottonseed oil, vegetable oil, peanut oil, soybean oil, palm oil, sesame oil, jojoba oil, coconut oil, mineral oil or any other edible, non-toxic oil. Preferably, the oil is cottonseed oil. Conidia spores harvested by water can be used immediately or stored until application preferably, under cool conditions of about 4° C. Conidia spores harvested by oil can be stored for up to a year, preferably about 6 months at room temperature (~25° C.). In general, conidia spores in the amount of about $10^7$–$10^8$ spore per prill may be obtained by cultivation of the prill in accordance with the process of the invention. For purposes of the invention the term "non-toxic oil" is used to mean any oil which does not have any adverse or chronic toxiological properties to humans.

It is also within the scope of the invention to add nutrients to the aqueous suspension or non-aqueous oil suspension of conidia spores before application to the targeted area of treatment. Such nutrients can enhance the germination of the conidia spores on the pests. Alternatively, it can be useful to pregerminate the conidia spores prior to application. Such pregermination can be easily established by stirring the harvested conidia spores in water for about 4–8 hours in a container or vessel or any other suitable means.

In another embodiment of the invention, the reactivated prill having the conidia spores attached thereto may be stored or packaged in a water-soluble polymeric container prior to harvesting the spores. To harvest the conidia spores, the water-soluble polymeric container having the reactivated prill contained therein is dissolved in water and the resulting emulsion is filtered to provide an aqueous suspension of conidia spores. Any polymeric material which is soluble in water, is inert to the fungal matter, and is capable of forming a container may be employed in the invention. Preferably, the polymeric material is a polyvinyl alcohol. The polymeric materials may be formed into a container using conventional methodology known in the container or packaging arts, such as, for example, by heat-sealing.

USE

The application of the dried prill, the reactivated sporulated prill, the harvested spores or the pregerminated spores prepared according to the invention is dependent on the nature of the pest to be controlled and the particular field of use (i.e., agriculture, horticulture, forest or mosquito control). If the pest target is a plant pest, the prill, the reactivated prill or harvested conidia spores can be applied near the plant or on the plant. If the target is a soil pest, the dried prill, the reactivated prill or the conidia spores can be applied to or mixed with the soil. If the target pests are mosquitos, the prill, the reactivated prill or the harvested conidia spores can be applied to the surface of the water. An important economic use of biopesticides of this invention is in controlling insects or pests during shipment of plants. Application of the biopesticides on infested plants prior to shipment will result in obtaining plants free of insects.

Different entomogenic fungi can be used in the biopesticide prill of the invention to control pests. Pests that can be controlled by the biopesticides of this invention include arthropods and nematodes. Particularly preferred pests include insects such as mosquitoes and blackflies and pests belonging to the acarina and arachnid family. The biopesticides are effective against pests which are normally sensitive and also those which are resistant to conventional pesticides. They are effective against all or individual pest development stages. The biopesticides can be used effectively against pests from the following: Isopoda, Oniscus asellus, Armadillidium, Diplopoda, Chilopoda, Symphyla, Thysanura, Collembola, Orthopera, Dermaptera, Isoptera, Anoplura, Mallophaga, Thysanoptera, Heteroptera, Homoptera, Lepidoptera, Coleoptera, Hymenoptera, Diptera, Siphonaptera, Arachnidia, and Acarina.

Also, the biopesticides can be used against plant parasitic nematodes including Meloidogyne spp., Pratylenchus spp., *Radopholus similes, Ditylanchus dipsaci,* Heterodera spp., Xiphenema spp., Globodera spp. and Hoplolaemus spp.

The principle target insect groups which are preferred for the biopesticides of this invention are: Culicidae (mosquitoes) and other Diptra, Aphidae (aphids), Dalphacidal (planthoppers), Cicadellidae (leafhoppers), Cercopidae (spittlebugs), Aleyodidae (white fly), Coccoidea (scales), Thysaoptera (thrips), Coleoptera (beetles), and Lepidoptera (caterpillars).

The prill dosage will vary greatly depending on the application. Factors to consider include the kind of prill formulation used (e.g., vermiculite prills are more efficient in controlling mosquito larvae than bran prills because of floating properties of the vermiculite prills), the kind of pest, the state of crop infested with the pest, the prevailing weather conditions, and the kind of the agriculture area (e.g., agriculture, horticulture, forestry or other conditions). In general, for controlling plant insects, an application dosage range from about $10^7$ conidia spores/ml to about $10^8$ conidia spores/ml is preferred. Such dosage can be easily obtained based on the following ratio: one gram of reactivated prill yields a suspension of $10^7$ conidia spores/ml in one liter. For controlling soil insects, an application dosage of about 1–10 kg, preferably about 5 kg Of inactivated and/or reactivated prill per hectare is preferred. The biopesticides can be applied by any convenient and conventional method including, broad cast spreading on the soil or plant, or mixed with the soil.

The method of applying the biopesticides of the invention will vary depending on the particular biopesticide used and on the intended use thereof. The dried prill and the reactivated prill may be applied by any conventional method known for applying dry granulated materials to the soil, water or plants. For example, the dried prill or the reactivated prill may be applied to the surface of soil and water by spraying or spreading using conventional apparatus. The dried prill and the reactivated prill may also be mixed into the soil for control of soilborne pests. Aqueous suspensions of the harvested conidia spores and the pregerminated conidia spores may be applied directly to the soil or plants using conventional methodology such as spraying, pouring, etc.

The examples which follow are given for illustrative purposes and are not meant to limit the invention described herein. The following abbreviations have been used throughout in describing the invention.

CFU—Colony forming unit
CPU—Conidia spores per prill unit
°C.—degree(s) Centigrade
g—gram(s)
hr—hour(s)
l—liter(s)
μ—micro
%—percent
lb—pound(s)
$ft^2$—square foot (feet)
M—molar
ml—milliliter
N—normal
PDA—peptone dextrose agar
RH—relative humidity
rpm—rotation per minute
w—weight
vvm—volume per volume per minute
AIS—Assessing Index Scale
GI—Growth Index

EXAMPLE 1

Production of Mycelium of *Paecilomyces fumosoroseous* in 20-Liter Batch Fermenter The fungus *Paecilomyces fumosoroseous* (ATCC 20874) was maintained on a slant agar containing 20 g/l malt, 20 g/l glucose, 1 g/l peptone, and 10 g/l agar. The slant was stored at 4° C.

Slants were transferred under sterile conditions to a shake flask medium of 30 g/l glucose, 20 g/l yeast extract, and 20 g/l corn steep liquor. The solution was adjusted to pH 6 before sterilization. After inoculation with the slant fungi, the shake flask containing the fungus was maintained at 30° C. for 24 hours on a round shaker at 300 rpm. The shake flask product, mainly blastospores, was used to inoculate a 20-liter fermenter containing 16 liters of production media composed of 60–80 g/l molasses, 20 g/l cotton seed flour, and 20 g/l corn steep liquor. The fermentation pH was controlled to pH 5.3 by adding base (2M NaOH). Aeration was maintained at between 0.8–1.0 vvm, and agitation was maintained at 400–600 rpm. In order to avoid formation of foam, 1.5 ml of Macol® P-2000 antifoam agent (Mazer® chemicals) was added to the fermentation solution. The fermentation was completed after 96–100 hours, and the filamentous mycelium was harvested by centrifugation. The yield of filamentous mycelium obtained was 30 g/l (dry weight).

EXAMPLE 2

Preparation of Biopesticide Formulations

The mycelium of *Paecilomyces fumosoroseous* obtained in Example 1 was used to prepare the formulations described in Table I. Briefly, the *Paecilomyces mycelium (*300 g at 25% moisture content) was blended and mixed with the described amounts of carriers. The carriers had been previously autoclaved for 1 hour at 121° C. with 1 liter of water. Sodium alginate was added and each of the blended mixtures was brought to a total volume of 3 liters and 1N NaOH was added to obtain the indicated pH. For prill formation of each mixture, a bath containing 5 liters of a calcium chloride solution at concentration range of 13–27% (pH 6.35–7.00) was used. The blended mycelium/porous carrier mixture was loaded onto a prilling column, and the mixture was added dropwise to the coagulation bath to form alginate prill. The prill were submerged in the coagulation bath for 1 hour or longer. The prill were easily removed from the bath by screening them through a metallic screen. The wet prill, which contain as much as 80–85% moisture, were loaded onto a fluidized bed dryer and dried at an air temperature below 30° C. The prill were dried to a water content of 6% to 10% w/w.

TABLE I

| Formulation | Porous Carrier | Amount | Alginate Amount | pH |
|---|---|---|---|---|
| A | Bran | 300 g | 60 g | 6.0 |
| | Milk Powder | 80 g | | |
| B | Bentonite | 500 g | 35 g | 8.5 |
| C | Vermiculite | 400 g | 70 g | 5.9 |
| D | Peat Moss | 350 g | 35 g | 8.5 |
| E | Vermiculite | 200 g | 60 g | 8.5 |
| | Bran | 200 g | | |
| | Cotton Seed Flour | 100 g | | |
| F | Vermiculite | 300 g | 45 g | 5.3 |
| | Bran | 100 g | | |
| G | Vermiculite | 300 g | 45 g | 9.0 |
| | Bran | 100 g | | |

EXAMPLE 3

Evaluation in vitro of Prill and Conidia Spore Viability

Batches of biopesticide prill prepared according to Example 2 were evaluated and assessed for viability, germination and conidiation after storage.

Prill Mycelium Viability

Thirty-six prill were rehydrated by submerging in water for 30 minutes. The reactivated prill were placed on the surface of an agar plate or empty plastic well and incubated for 48 hours at room temperature. The percent viability of the prill was evaluated by observing and tracking the mycelium developed on the surface of the prill. Table II represents percent prill viability of different batches which were stored at different temperatures for up to 12 months.

TABLE II

| Formulation | Storage Temperature | Storage Time (months) | Prill Viability |
|---|---|---|---|
| D | 4° C. | 6 | 100% |
| D | 25° C. | 6 | 99% |
| A | 4° C. | 6 | 100% |
| A | 25° C. | 6 | 99% |
| A | 4° C. | 5 | 98% |
| A | 25° C. | 9 | 95% |
| A | 25° C. | 12 | 95% |
| A | 4° C. | 12 | 95% |
| B | 4° C. | 11 | 100% |
| C | 4° C. | 12 | 100% |
| F | 4° C. | 6 | 100% |
| G | 4° C. | 6 | 100% |

Conidiation of Mycelium Prills In Vitro Test

Conidiation of the different prill formulations which sporulated on agar plates or empty plastic wells for 48 hours as above were examined by transferring three sporulated prill to a sterile screw cap tube containing 10 ml of a 0.01% Tween™ 80 surfactant solution. The tube was shaken vigorously for 20 seconds and the conidia spores were counted using a hemacytometer. Table III represents spore counts for prill which were stored at different temperatures for as up to 11 months. All conidia spores germinated to 100%.

TABLE III

| | Conidiation at Different Temperatures: | | |
|---|---|---|---|
| Formulation | Storage Temperature | Storage Time (months) | Conidiation (Spore per Prill) |
| A | 4° C. | 10 | $1.95 \times 10^7$ |
| A | 25° C. | 10 | $1.07 \times 10^7$ |
| A | 25° C. | 11 | $1.33 \times 10^7$ |
| C | 25° C. | 6 | $5.0 \times 10^7$ |
| F | 25° C. | 6 | $1.87 \times 10^7$ |

Conidia Spore Germination In Vitro Test

The conidia spores which were produced in the preceding section by the sporulated prill were collected and a $1 \times 10^5$ spore per ml solution was prepared. Sterile sabourads dextrose broth (100 μl) was added to 2 rows of a 96 well plate (Corning 25860 polystyrene). The spore suspension (100 μl) was added to a total of 16 wells of each plate. The spores were incubated at 28° C. for 24 hours and were examined for germination (forming germ tube). All prill formulations tested produced 100% germination of the conidia spores under the various storage conditions and times.

EXAMPLE 4

Efficacy Study

The efficacy of the bran/milk biopesticide prill formulations prepared in Example 2 was evaluated in a greenhouse for control of whiteflies. Each test was conducted by infesting a blue salvia plant with whiteflies. The insects were allowed to oviposit for 24 hours, then all adults were removed. The salvia were grown under greenhouse conditions allowing the immature whitefies to develop. Several early to mid-forth instar scales were removed and incubated in 100% relative humidity to demonstrate that no viable *Paecilomyces fumosoroseous* fungi were present in the greenhouse. The infested plants were then subjected to the following treatments:

Treatment A—1 g of prill per plant was scattered directly on the moistened surface of the soil.

Treatment B—1 g of prill per plant was soaked for 1 hour in deionized water. The prill were placed in a petri dish atop 1 piece of moistened Whatman™ 5-filter paper and incubated for 24 hours. The prills were then scattered directly on the soil surface.

Treatment C—10 prill were incubated on a PDA agar plate for 7 days at 25° C. under a 12-hour photo period. The plate was scraped with a sterile instrument. Five ml of this solution were pipetted into 500 ml of a 2% sucrose solution. Plants were dipped in this solution.

Treatment D—Plants were dipped in 500 ml of deionized water (no prill added).

Eight plants were used per treatment. Living, dead, and infected scales were counted on 3 leaves per plant weekly. Each week, 24 instar scales were removed from leaves in each treatment and incubated in 100% RH to measure mortality. Table IV represents the mortality and efficacy results.

TABLE IV

| Treatment Type | Percent of Infected Whitefly Day 3 | Percent of Infected Whitefly Day 7 |
|---|---|---|
| Treatment A | 60% | 94% |
| Treatment B | 48% | 58% |
| Treatment C | 40% | 60% |
| Treatment D | 18% | 18% |

EXAMPLE 5

In Vivo Bio Assay (Reactivation of Prill)

A standard in vivo bio assay to assess the viability and infectivity of the conidia spores produced by the prills has been developed. The procedure consists of harvesting conidia spores from activated prills by means of soaking the prills in 0.05% Tween™ 80 solution and then diluting the conidia spores harvested to obtain a concentration of $1.0\times10^7$ conidia spores per 1 ml which was used to assess efficacy.

Germination (Viability) Assays

The conidia spore suspension was spread over a sterile microscope slide coated with a thin layer of water agar (2.0% Difco agar) by means of a sterile inoculating loop. Slides were then placed into wet chambers (petri dishes with filter paper) and 0.2 ml of sterile water was added to the filter paper. Conidia spores were incubated for 16 hours in an incubator (25° C.) and assessed for germination under a light microscope. All conidia spores with a germ-tube(s) of any size were counted as being germinated.

Infectivity Assay

The sweet potato whitefly *B. tabaci* was the host insect used for measuring infectivity. Early 4th instar nymphs of *B. tabaci* (un-synchronized population reared on Hibiscus sp) were collected from leaves with a flattened needle and placed on the surface of a sterile microscope slide. Conidia spore suspension which was prepared as described above was used by placing a drop with known concentration on the surface of a sterile microscope slide (20 drops per slide, 10 in each of two rows running the length of each slide). Previously collected nymphs of *B. tabaci* were placed on each droplet and into a wet chamber and 0.2 ml of sterile water were added to the filter paper. Samples were kept in an incubator (25° C.) for a period of 7 days. Two chambers (total of 40 nymphs) were used for each sample tested. As a control, slides with nymphs only were prepared by the same manner as previously described but without conidia spores added to the Tween 80 solution. To evaluate the growth of the fungus without nutrient source, slides with drops of conidial suspension only (without nymphs) were also prepared.

Each nymph or drop of conidia spore was observed under a light microscope (100×magnification) and rated according to the following index (Assessing Index Scale="AIS"):

0.0—No changes (conidia spores do not germinate, no visible changes anywhere in the drop area)

0.5—Germination of conidia spores (beginning of germination, conidia spores with one or two germ-tubes are present anywhere in the drop area or unbranched hyphae are present)

1.0—Beginning of mycelial growth (anywhere in the drop area presence of branched hyphae is visible, no growth of fungus on host is noted)

1.5—First occurrence of the fungus hyphae on the host (anywhere on the host surface hyphae of fungus are present)

2.0—the surface or alongside of host body overgrowth by Regular growth of mycelium on the host (on most of mycelium is visible)

2.5—First occurrence of newly formed conidia spores (anywhere on the host surface or on a mycelium alongside the host body first conidiophores and newly formed conidia spores in chains are present)

3.0—Regular sporulation (fully sporulated mycelium covers most of the surface of infected host or takes place alongside of host)

All samples were rated on days 1,3,5, and 7. The results were expressed as a daily average of "AIS" from each sample (40 nymphs). Control nymphs were assessed with the developmental stage of the nymph and presence of any infection being recorded. Control drops (no nymphs of *B. tabaci* placed into the drop) were observed and the developmental phase of fungus noted (germination of conidia spores, mycelial growth, or sporulation).

Basic physical characteristics of different types of alginate prill used in the experiment are presented in the following table.

TABLE V

| Formulation | Avg Wt of 1 prill (g) | Avg Amt of prills per 1 g | Shape of prills |
|---|---|---|---|
| G | 0.0027 | 370 | homogenous |
| D | 0.0025 | 400 | homogenous |
| C | 0.0035 | 286 | diverse |
| E | 0.0037 | 270 | homogenous |
| E | 0.0030 | 333 | homogenous |
| E | 0.0017 | 590 | homogenous |
| E | 0.0014 | 714 | homogenous |

*The E formulations differ by date of manufacture.

Visual and physical weight changes which occur during activation are shown in Table VI.

TABLE VI

| Formulation | Initial weight (g) | Day 1 wt (g) | Day 1 change (%) | Day 2 wt (g) | Day 2 change (%) | Day 7 wt (g) | Day 7 change (%) |
|---|---|---|---|---|---|---|---|
| F | 0.0027 | 0.0039 | +44.4 | 0.0042 | +55.6 | 0.0046 | +70.4 |
| G | 0.0025 | 0.0040 | +60.0 | 0.0044 | +76.0 | 0.0050 | +100.0 |
| D | 0.0035 | 0.0048 | +37.1 | 0.0056 | +60.0 | 0.0065 | +85.7 |
| C | 0.0037 | 0.0053 | +43.2 | 0.0055 | +48.6 | 0.0046 | +24.3 |
| E | 0.0030 | 0.0047 | +56.7 | 0.0050 | +66.7 | 0.0063 | +110.0 |
| E | 0.0017 | 0.0033 | +94.1 | 0.0035 | +105.9 | 0.0032 | +88.2 |
| E | 0.0014 | 0.0027 | +92.9 | 0.0029 | +107.1 | 0.0026 | +85.7 |

Table VII Compares different types of alginate pellets with incorporated mycelium of entomogenous fungus *Paecilomyces fumosoroseus* isolate PFR 97—an average growth index during activation of prills in laboratory conditions (counted as an average GI from 20 prills*).

TABLE VII

| Formulation | GI - Day 1 | GI - Day 3 | GI - Day 5 | GI - Day 7 |
|---|---|---|---|---|
| F | 1.8 | 3.4 | 4.6 | 5.0 |
| G | 1.1 | 3.3 | 4.4 | 5.0 |
| D | 1.4 | 3.6 | 4.1 | 5.0 |
| C | 0.8 | 1.8 | 3.8 | 5.0 |
| E | 2.0 | 3.6 | 4.4 | 5.0 |
| E | 1.8 | 3.0 | 4.2 | 5.0 |
| E | 1.7 | 3.2 | 4.4 | 5.0 |

*Growth index scale:
0 — no visual changes on prills
1 — swelling phase (change of size, shape and color, no growth of fungus noted)
2 — first hyphae growth on surface of prills
3 — regular overgrowth, mycelium covers most of the prill's surface
4 — beginning of sporulation (first conidiophores and conidial chains)
5 — full sporulation (most of the prill's surface covered with sporulated mycelium)

Production of conidia spores and germination of Formulation E over 7 day period after activation is described in Table VIII.

TABLE VIII

| Time of Activation | An Average Amount of Conidia Spores per 1 Prill | Germination Test: % Germination | Germination Test: Shape of Germinated Conidia Spores |
|---|---|---|---|
| Day 2 | $1.42 \times 10^6$ | 93.7 | 2 germ - tubes |
| Day 3 | $1.29 \times 10^7$ | 98.8 | 2 germ - tubes |
| Day 4 | $1.50 \times 10^7$ | 100 | 2 germ - tubes |
| Day 5 | $2.97 \times 10^7$ | 100 | 2 germ - tubes |
| Day 7 | $3.31 \times 10^7$ | 100 | 2 germ - tubes |
| Day 10 | $3.37 \times 10^7$ | 99.2 | 2 germ - tubes |

Comparison of different types of prills for germination is shown in Table IX.

TABLE IX

| Formulation | % Germination | Dominant Shape of Germinating Conidia Spores |
|---|---|---|
| F | 99.8 | 2 long germ-tubes (*) |
| G | 99.2 | 1 long germ-tube |
| D | 93.3 | 2 short germ-tubes |
| C | 81.6 | 1 short germ-tube |
| E | 99.6 | 2 long germ-tubes (*) |
| E | 99.7 | 2 long germ-tubes (*) |
| E | 99.0 | 2 long germ-tubes (*) |

(*) - first secondary branches presents

Infectivity of the conidia spores produced from Formulation E after different periods of activation is described in Table X.

TABLE X

| Period of Prills Activation | Average "AIS" Day 1 | Average "AIS" Day 3 | Average "AIS" Day 5 | Average "AIS" Day 7 |
|---|---|---|---|---|
| 2 days | 0.75 | 0.90 | 1.20 | 1.85 |
| 3 days | 0.80 | 1.35 | 1.75 | 2.15 |
| 4 days | 0.85 | 2.15 | 3.00 | 3.00 |
| 5 days | 0.90 | 2.30 | 3.00 | 3.00 |
| 7 days | 0.80 | 2.15 | 3.00 | 3.00 |
| 10 days | 0.65 | 1.90 | 2.70 | 3.00 |

*Assessing Index Scale - "AIS
0.0 No changes (conidia spores do not germinate, no any visible changes anywhere in a drop area)
0.5 Germination of conidia spores (beginning of germination, conidia spores with one or two germ-tubes are present anywhere in a drop area or unbranched hyphae are present)
1.0 Beginning of mycelial growth (anywhere in a drop area presence of branched hyphae is visible, no growth of fungus on host is noted)
1.5 First occurrence of the fungus hyphae on the host (anywhere on the host surface a hyphae of fungus are present)
2.0 Regular growth of mycelium on the host (on most of the surface or alongside of host body overgrowth by mycelium is visible)
2.5 First occurrence of newly formed conidia spores (anywhere on the host surface or on a mycelium alongside the host body first conidiophores and newly formed conidia spores in chains are present)
3.0 Regular sporulation (fully sporulated mycelium covers most of the surface of infected host or takes place alongside of host)

Comparison of different type of prill for infectivity is described in Table XI.

TABLE XI

| Formulation | "AIS"-Day 1 | "AIS"-Day 3 | "AIS"-Day 5 | "AIS"-Day 7 |
|---|---|---|---|---|
| F | 0.95 | 2.30 | 3.00 | 3.00 |
| G | 0.85 | 2.00 | 2.60 | 3.00 |
| D | 0.70 | 1.90 | 2.30 | 2.80 |
| C | 0.45 | 1.60 | 2.20 | 2.70 |
| E | 0.80 | 2.15 | 2.55 | 3.00 |
| E | 0.85 | 2.35 | 3.00 | 3.00 |
| E | 0.90 | 2.40 | 3.00 | 3.00 |

EXAMPLE 6

In order to compare the germination and infectivity of the conidia spores produced by the prill to standard conventional methods of growing conidia spores on different substrate, the following experiment was conducted. Three (3) samples of conidia spores were obtained from 3 different sources:

1) from prills (formulation E),
2) from agar petri dishes (PDA—Potato Dextrose Agar Difco), and
3) from whitefly nymphs infected with PFR.

In all experiments, conidia spores of strain PFR ATCC 20874 were used.

The conidia spores from prills were harvested as previously described. The PDA-conidia spores were obtained from surface cultures on a solid artificial media. PDA plates were inoculated with 1 ml of conidial suspension ($1.0 \times 10^7$ per ml), spread over the entire surface of the plate and kept an incubator (25° C.).

When harvested on day 20, conidia spores from the surface of the culture were washed with sterile 0.05% Tween 80 surfactant and this suspension was diluted to a concentration of $1.0\times10^7$ conidia spores per 1 ml. The total amount of conidia spores produced on a surface cultures (PDA plates) was stated by the similar procedure as from activated prills. For the same experiment, conidia spores harvested from infected hosts (*B. tabaci*, early $4^{th}$ instar nymphs) were used. The same method as for standard bioassay (described below) was used to obtain infected nymphs. Infected nymphs on which the fungus was sporulating were collected and placed into plastic ampules and soaked into 1 ml of sterile 0.05% Tween 80 solution. The suspension of conidia spores obtained in this manner was diluted to a concentration of $1.0\times10^7$ conidia spores per 1 ml. The total length (from tip of germ tube to the tip of the opposite one, if present) of at least 250 conidia spore was measured using an ocular micrometer. The following table presents the viability and virulency of conidia spores obtained from PFR strain ATCC 20874 which was obtained from different nutrient sources.

As can be seen from Table XII, the conidia spores obtained from the prill have a higher infectivity than those produced on the surface of the PDA culture. The time to obtain conidia spores on the PDA culture is twice as long as obtaining conidia spores from prills.

TABLE XII

| Nutrient Source | % Germination | Dominant Shape and Length of Germinating Conidia Spores | "AIS" Day 1 | "AIS" Day 3 | "AIS" Day 5 | "AIS" 7 day |
|---|---|---|---|---|---|---|
| Formulaion E | 99.3 | 2 germ-tubes (4.4-5.8 um | 0.90 | 2.10 | 3.00 | 3.00 |
| PDA | 93.8 | 1 germ-tube (3.0-3.8 um) | 0.75 | 1.85 | 2.60 | 3.00 |
| *B. tabaci* E4 nymphs | 99.8 | 2 germ-tubes (8.2-11.2 um) | 0.95 | 2.20 | 2.90 | 3.00 |

EXAMPLE 7

In order to evaluate the ability of PFR prill to sporulate and germinate in soil, the following experiment was conducted. Eight 250 ml Erlenmyer glass flasks were filled with 15 g of Redi lite soil mix (Terra-Lite ®). The flask and the soil were autoclaved for 20 minutes at 121° C. After the soil was cooled to room temperature, 20 vermiculite prill (as prepared and described in Example 2) were added to the soil mixture in the flask. The soil and the prill were shaken well, and 50 ml of sterile deionized water was added to enhance humidity. The soil prill mixture was incubated at 25° and 30° C. After a month the number of spores in the soil were evaluated. The spore count was determined by the following method:

CFU Determination

1. Aseptically mixed thoroughly the flask contents using a sterile spoonula.
2. Carefully removed 1 g of wet soil mixture.
3. Made 1:10 serial dilutions using 50 mM phosphate buffer pH 7.0.
4. Plated the sample by adding 100 μl of sample onto a Rose Bengal plus 100 mg chlorampenicol plate and make a spread plate. Prepare triplicate plates.
5. Incubated the plates at 28° C.
6. After 5 to 6 days counted the fungal colonies present.

Table XIII represents the results of this study.

TABLE XIII

| Flasks | CFU/g after 30 Days Incubation Temperature 25° C. | 30° C. |
|---|---|---|
| Flask 1,2 | $2.48\times10^6$ | $2.2\times10^6$ |
| Flask 3,4 | $2.0\times10^5$ | $2.6\times10^6$ |
| Flask 5 | $2.6\times10^6$ | — |

EXAMPLE 8

Large Scale Protection of Hibiscus Against White Fly

Figure 2:
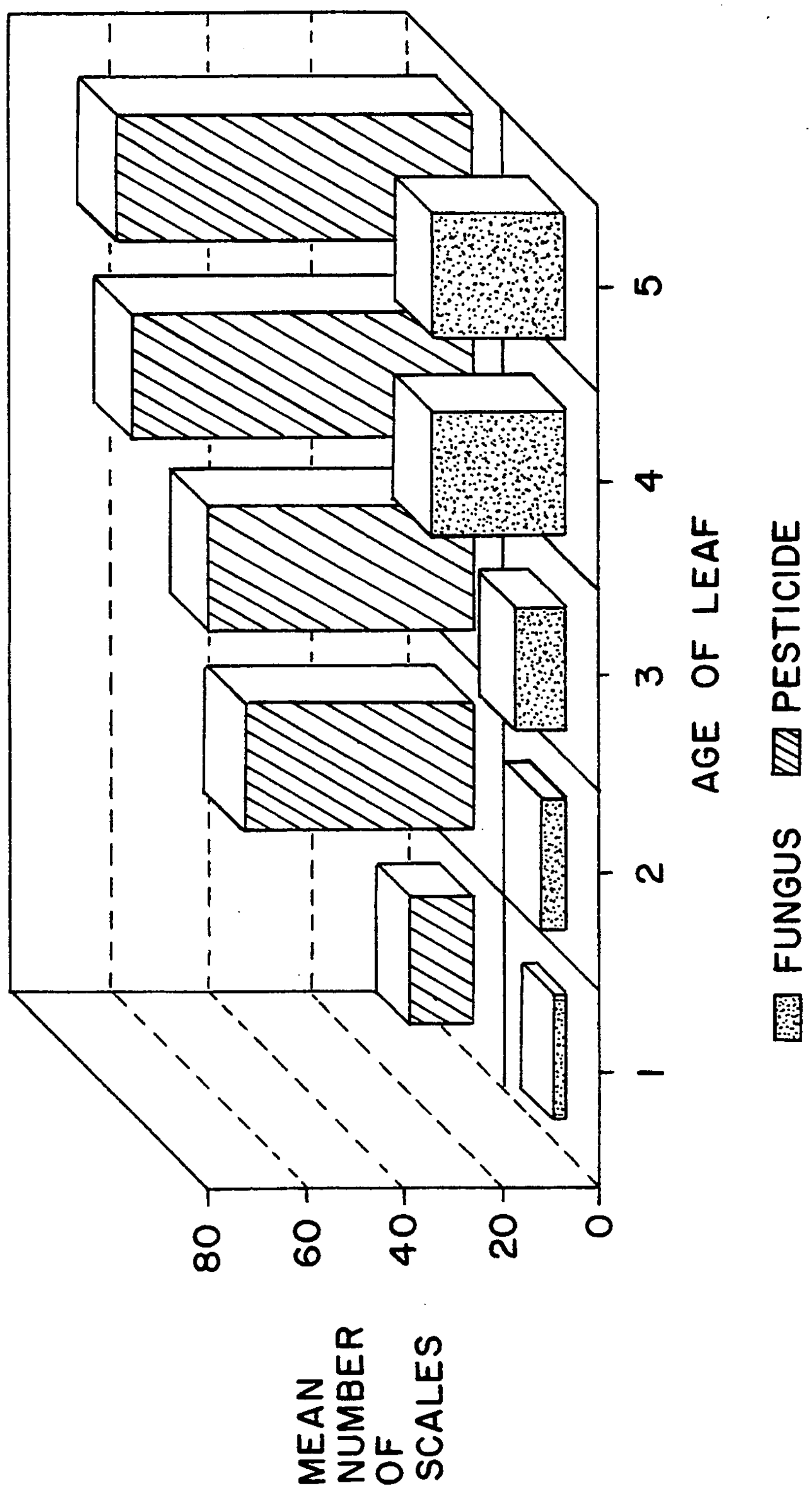
FIG. 2 compares the ability of the formulation of the invention with that of chemical treatments to effect whitefly scales.
Figure 3:
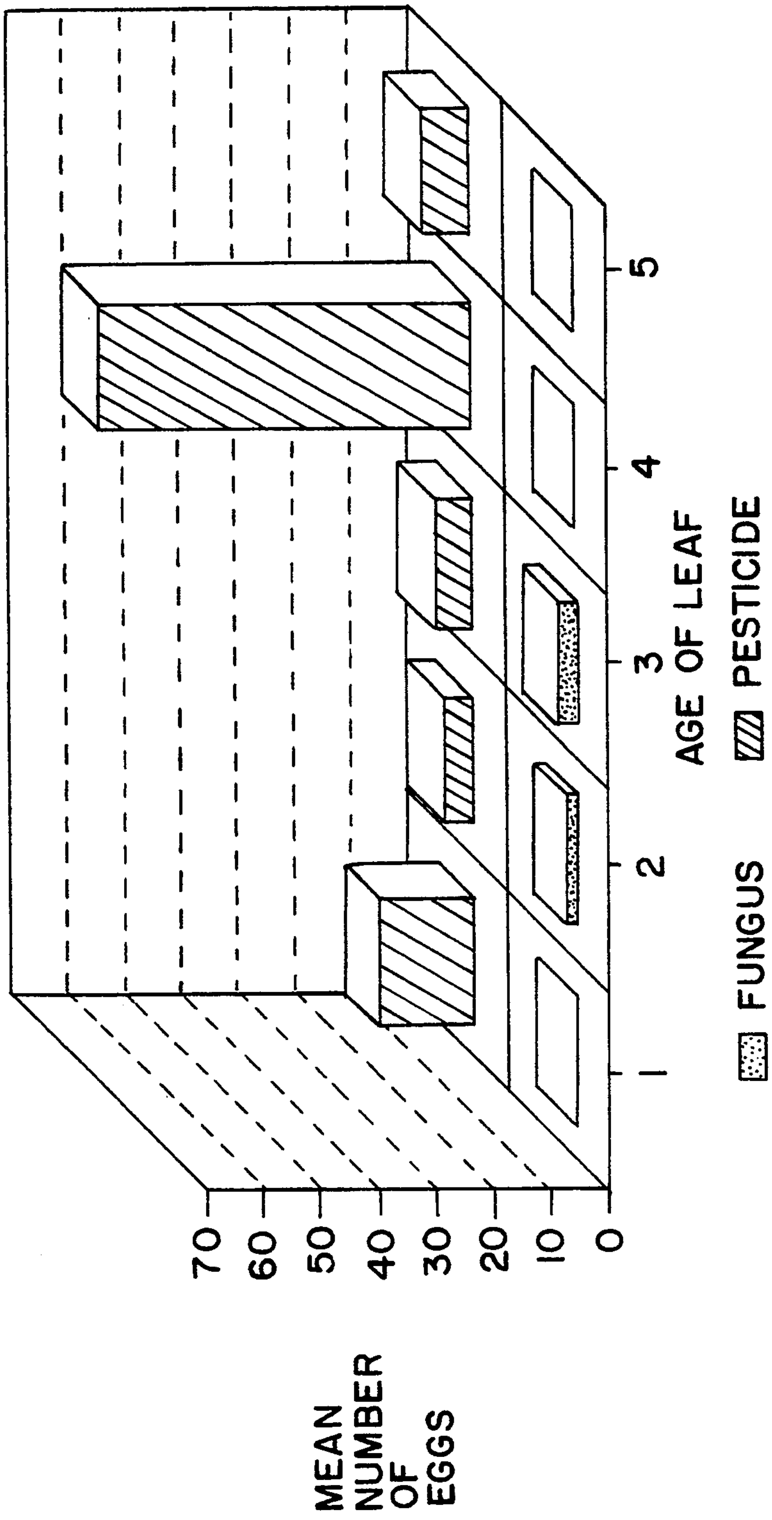
FIG. 3 compares the ability of the formulation of the invention with that of chemical treatments to effect whitefly eggs.

The PFR conidia spores harvested from reactivated prills were tested to evaluate the ability to protect hibiscus sp. plants against white fly (*Bemisia tabaci*). The reactivated prill described in Example 5 were used to protect hibiscus plants grown in commercial greenhouses in Apopka, Fla. Large quantities (100 g) of dried prill were activated in large plastic boxes (450×250×100 mm). The same procedures for evaluating and cultivating the prill as described in Example 5 were used. Briefly, after 7 days incubation at 25° C., the conidia spores produced were stored at 4° C. About 3-6 hours prior to application, 10 g of the spores were harvested from the reactivated prill into 2 liters of water plus 0.05% Tween 20 ® surfactant (obtained by Fisher Scientific, Fairlawn, N.J.). The concentration of conidia spores in this concentrate was counted using a Neubaer hemocytometer. Prior to application, the conidia spore concentrate was diluted with water to a final concentration of $1.0-1.5\times10^7$ conidia spores/mi. Fifty liters of the final conidia spore suspension were applied in one treatment to 800 hibiscus plants using a backpack sprayer (Birchmeier) with special attention to cover the underside of the leaves. The biopesticide was applied weekly for a period of one month. As a control, Hibiscus plants were treated with different chemical agents (see Table for chemical application). Plants were checked once a week, and leaves were examined randomly from the chemical control and from the PFR treatment. FIGS. 2-4 show the comparison of the treated plant with PFR to a control area which was treated with chemicals. As can be seen from the figures, PFR works better than the chemical treatment. It is important to note that parasitized scales were found mainly in the chemical treatment and not at the PFR site. However, no parasites infected with PFR were found. Therefore, mortality of whitefly at the PFR treated area is mainly because of the fungus establishment.

EXAMPLE 9

Pregermination

Conidia spores harvested from reactivated prill described in Example 5 (Formulation E) were evaluated to determine whether pregermination of conidia spores or addition of stimulating nutrient to the conidia spores can enhance the infectivity of the conidia spores. The conida were applied to plants infected with whiteflies.

The results shown in Table XIV indicate that pregerminated conidia spores have the greatest effectiveness in controlling whitefly within the shortest time (12-24 hours).

TABLE XIV

| Time at 100% humidity directly after Application* | Percent of Dead Whitefly: | | |
|---|---|---|---|
| | Formulation E in Water | Formulation E with Nutrient | Formulation E Pregerminated |
| 12 | 64 | 72 | 84 |
| 24 | 56 | 77 | 82 |
| 48 | 47 | 91 | 89 |
| 72 | 68 | 94 | 90 |

*Subsequently switched to 75% humidity

EXAMPLE 10

Induced Resistance

The conidia spores of the invention were tested to determine the influence of the entomogenous fungus *Paecilomyces fumosoroseus* on the colonization and induced resistance of host plants. A total of 60 uninfested poinsettia plants of the same size and shape (an average of 6 leaves/plant) grown in small pots were used. Adult sweetpotato whiteflies were caught into plastic tubes and released onto the treated plants. The plants were treated with *Paecilomyces fumosoroseus* PFR 97 harvested from alginate pellets (Formulation E activated as described in Example 5). The conidial suspension used was a 0.05% Tween solution adjusted to a titre of $1.0\times10^7$ conidia spores per ml.

The treatments used were:

A—preventive treatment (plants were treated with conidial suspension one week before exposure to sweetpotato whitefly adults. Before whitefly adults were released, the treated plants were deposited into a nylon cage to prevent any undesirable infestation);

B—treatment before release of whitefly adults (plants were treated with conidial suspension and then exposed to the whitefly adults when the surface of treated plants dried);

C—Control plants (plants were treated with 0.05% Tween solution and then exposed to the whitefly adults when the surface of treated plants dried).

All treated plants were placed in a greenhouse in a randomized square fashion. Twelve plants from each of the variants (A-B-C) were placed in a randomized square and adults of whitefly were released at 5 points (center of the square and each of the corners in the second row).

The number of adults per plant was determined every 24 hrs for a period of 1 week. When counted, the following data were noted:

a) alive adults (total amount per all plants in each group)

b) dead adults (total amount per all plants in each group)

c) infected adults (total amount per all plants in each group)

Treatment of plants with *Paecilomyces fumosoroseus* ATCC 20874 conidia spores harvested from prills resulted in significantly poorer establishment of pest populations when treated 1 week before exposure than when treated just prior or not at all. Treatment just prior to exposure was better than not at all. These results shown in Table XV indicate that conidia spores of *Paecilomyces fumosoroseus* ATCC 20874 harvested from prills illicit an immune response (induced resistance) by the plant.

TABLE XV

| Day | Total number of alive adults | Variant A number/% | Variant B number/% | Variant C number/% |
|---|---|---|---|---|
| 1 | 1157 | 238/20.6 | 336/29.0 | 583/50.4 |
| 2 | 1146 | 170/14.8 | 379/33.1 | 597/52.1 |
| 3 | 967 | 130/13.4 | 298/30.8 | 539/55.8 |
| 4 | 697 | 71/10.2 | 186/26.7 | 440/63.1 |
| 5 | 447 | 34/7.6 | 93/20.8 | 320/71.6 |
| 6 | 315 | 19/6.0 | 70/22.2 | 226/71.8 |
| 7 | 270 | 23/8.5 | 63/23.3 | 184/68.2 |
| 14 | 68 | 10/14.7 | 22/32.4 | 36/52.9 |

EXAMPLE 11

Preparation of Aqueous Suspension of Conidia Spores Using Water-Soluble Container of Reactivated Prill Mycleium of the Fungus *Paecilomyces fumosoroseus* (ATCC 20874) was produced as described in Example 1. The mycelium obtained was formulated with a porous carrier and nutrient in the following ratio: 20% Bran; 20% vermiculate, 20% cotton Seen Floure (CSF) and 50% of mycelium. Formulated prill were obtained and dried as described in Example 2. One hundred (100) grams of the prills were further activated as described in Example 5. Following a rich, full sporulation, after 7 days the activated prill was dried by placing them in a box at room temperature (25° C.) and a relative humidity of 10-20%.

After 10 days of storage, 10 grams of the dried reactivated prill were placed in a polyvinyl alcohol release film (obtained from Chris Craft Industrial Products, Inc.) 60×60 mm, and the film was heat-sealed to produce a bag using an Electronic Impulse Autosealer Type 450 by TEW Electric Heating Equipment Co., LTD. The bag was then introduced into a water bath containing 100 ml of distilled water with 0.05% surfactant (Tween 80® obtained from Fisher Scientific of Fairlawn, N.J.). The bath was agitated using a magnetic stirrer. After 1 hour of mixing the content of the bath was examined. The polymeric bag was completely dissolved to yield a suspension of conidia spores. The suspension was filtered to remove portions of the prill which were not dissolved. The number of spores per ml of the suspension was $1.1\times10^8$, as determined by counting spores under a light microscope (100× magnification).

We claim:

1. An improved stable, dried, prilled biopesticidal composition comprising an inert carrier which is capable of supporting fungal growth and promoting conidia sporulation, and an entomogenous fungal biomass at least about 80% of which is in the form of mycelium and is prepared by submerged fermentation of the fungus, *Paecilomyces fumosoroeus* isolate ATCC No. 20874.

2. The biopesticidal composition of claim 1 wherein the fungus has been treated to produce conidial spores.

3. The biopesticidal composition of claims 1 or 2 wherein at least about 90% of the biomass is in the form of mycelium.

4. The biopesticidal composition of claims 1 or 2 wherein the mycelium is filamentous in form.

5. The biopesticidal composition of claims 1 or 2 which further comprises a nutrient.

6. A process for preparing an improved fungal biopesticide for control of insect and nematode infestation comprising (a) fermenting a fungus *Paecilomyces fumosoroseus* isolate ATCC No. 20874 in a culture medium by submerged fermentation to produce biomass such that at least 80% of the biomass is in the form of mycelium;

(b) harvesting the biomass;

(c) mixing the biomass with a carrier;

(d) forming prill from the biomass/carrier mixture;

(e) optionally, drying the prill;

(f) treating the prill to produce pathogenic conidia spores; and (g) harvesting the conidia spores from the treated prill.

7. An improved biopesticidal formulation for controlling insect and nematode pests comprising conidial spores of the fungus *Paecilomyces fumosoroseus* isolate ATCC 20874 wherein said conidial spores have been prepared from a stable, dried, prilled biopesticidal composition comprising an inert carrier which is capable of supporting and promoting growth of the fungus and a biomass of the fungus, at least 80% of which biomass is in the form of mycelium, wherein the fungal biomass is prepared by submerged fermentation.

8. The biopesticidal formulation of claim 7 wherein the conidial spores have been pregerminated to produce germ tubes.

9. The biopesticidal formulation of claim 7 which further comprises a mammalian non-toxic oil.

10. The biopesticidal formulation of claim 9 in which the oil is selected from the group consisting of cottonseed oil, vegetable oil and mineral oil.

11. The process of claim 6 which further comprises the following step:

(i) pregerminating the harvested conidia spores.

12. The process of claim 6 wherein at least about 90% of the biomass is in the form of mycelium.

13. The process of claim 6 wherein the mycelium is filamentous in form.

14. The process of claim 6 wherein the conidia spores are harvested by washing the treated prill with water or a non-aqueous, non-toxic oil.

15. The process of claim 14 wherein the non-toxic oil is selected from cottonseed oil, vegetable oil, peanut oil, palm oil, sesame oil, jojoba oil, coconut oil, soybean oil or mineral oil.

16. A fungal biopesticide prepared by the process of claims 11, 14, or 6.

17. The biopesticide of claim 16 which is effective for the control of insect and arachnid infestation.

18. The biopesticide of claim 17 which is effective for the control of infestation by whiteflies, mosquitos, aphids, planthoppers, leafhoppers, spittlebugs, mites, scales, thrips, beetles or caterpillars.

19. The biopesticide of claim 16 which is effective for the control of nematode infestation or plant damage incurred by nematodes.

20. A method for controlling insect and nematode infestation of a treatment area comprising applying a pesticidally effective amount of the biopesticide of claim 16 to the area.

* * * * *

UNITED STATES PATENT AND TRADEMARK OFFICE

CERTIFICATE OF CORRECTION

PATENT NO. : 5,360,607

DATED : November 1, 1994

INVENTOR(S) : Eyal et al

It is certified that error appears in the above-indentified patent and that said Letters Patent is hereby corrected as shown below:

On the title page, item [73] Assignee, following "N.Y.", insert --and the University of Florida, Gainesville, FL--.

Signed and Sealed this

Twenty-sixth Day of December, 1995

Attest:

BRUCE LEHMAN

Attesting Officer

Commissioner of Patents and Trademarks